United States Patent [19]
Turner

[11] Patent Number: 5,638,812
[45] Date of Patent: Jun. 17, 1997

[54] COATED MEDICO-SURGICAL DEVICES

[75] Inventor: Mark William Turner, Folkestone, England

[73] Assignee: Smiths Industries PLC, London, England

[21] Appl. No.: 680,616

[22] Filed: Jul. 16, 1996

[30] Foreign Application Priority Data

Aug. 15, 1995 [GB] United Kingdom ............... 9516658

[51] Int. Cl.6 ..................................... A61K 38/47
[52] U.S. Cl. ........................ 128/207.14; 424/94.61
[58] Field of Search .............. 128/207.14; 424/94.61; 435/206, 180, 181, 176

[56] References Cited

U.S. PATENT DOCUMENTS

| 5,001,062 | 3/1991 | Larsson et al. | 435/176 |
| 5,433,705 | 7/1995 | Giebel et al. | |
| 5,458,876 | 10/1995 | Monticello | 424/94.61 |

FOREIGN PATENT DOCUMENTS

WO87/07156  12/1987  WIPO.

Primary Examiner—Vincent Millin
Assistant Examiner—Robert N. Wieland
Attorney, Agent, or Firm—Pollock, Vande Sande & Priddy

[57] ABSTRACT

A tracheal tube or other medico-surgical device has a surface coating containing lysozyme enzyme, which is effective to reduce the build-up of bacteria on the tube.

4 Claims, 1 Drawing Sheet

COATED MEDICO-SURGICAL DEVICES

BACKGROUND OF THE INVENTION

This invention relates to medico-surgical devices.

Medical breathing circuit components, such as tracheal tubes, have a tendency to accumulate secretions that build up into a layer or biofilm. Other catheters, such as urethral catheters also accumulate a biofilm layer. This biofilm is a slimy layer comprised of bacteria in a protective coating of glycoproteins. Once the film has established it is difficult to remove because the glycoproteins and changes in physiology protect the bacteria from the action of antibiotics and disinfectants. It has been proposed, in GB-A-2270845, to coat a suction tube with an antimicrobial film so as to prolong the life of the tube. Alternatively, the device can be coated with a low friction layer to reduce the ability of secretions to cling to the device. Although these proposals can help reduce the build-up of biofilm they are not entirely effective in overcoming the problem.

BRIEF SUMMARY OF THE INVENTION

It is an object of the present invention to provide a medico-surgical device that is less prone to the accumulation of biofilm.

According to one aspect of the present invention there is provided a medico-surgical device having a surface layer of a substance including lysozyme.

The device may be a medico-surgical tube such as a tracheal tube. The surface layer may be a coating on the inside of the tube. The device may be a tracheal tube with a cuff around the outside of the tube close to the patient end, the tube having a surface layer of a substance including lysozyme extending along the outside surface at least above the cuff so as to reduce the build-up of bacteria in the trachea above the cuff. Alternatively, the tube may be a urethral catheter and the surface layer be a coating on the outside of the catheter.

According to another aspect of the present invention there is provided a medical tube having a layer on a surface of a substance containing an enzyme effective to reduce the build-up of bacteria on the tube.

A tracheal tube according to the present invention, will now be described, by way of example, with reference to the accompanying drawings.

DETAILED DESCRIPTION OF THE PREFERRED EMBODIMENT

Figure 1:
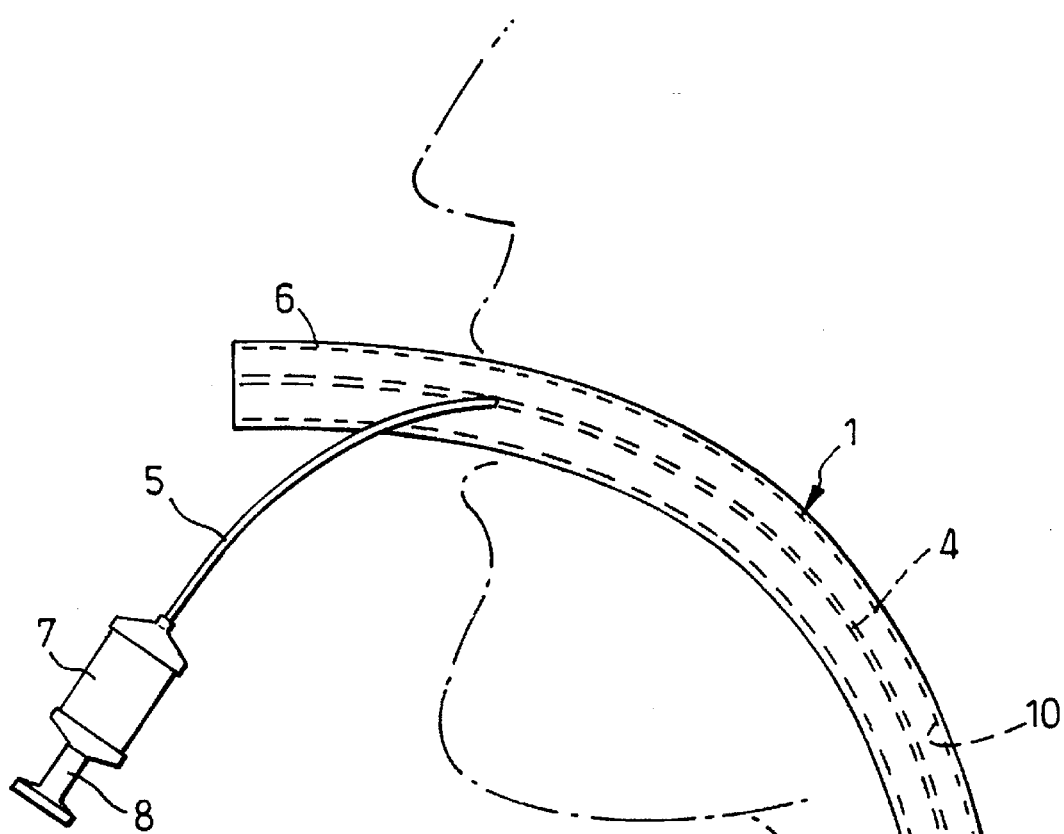
FIG. 1 is a side elevation view of the tube.
Figure 2:
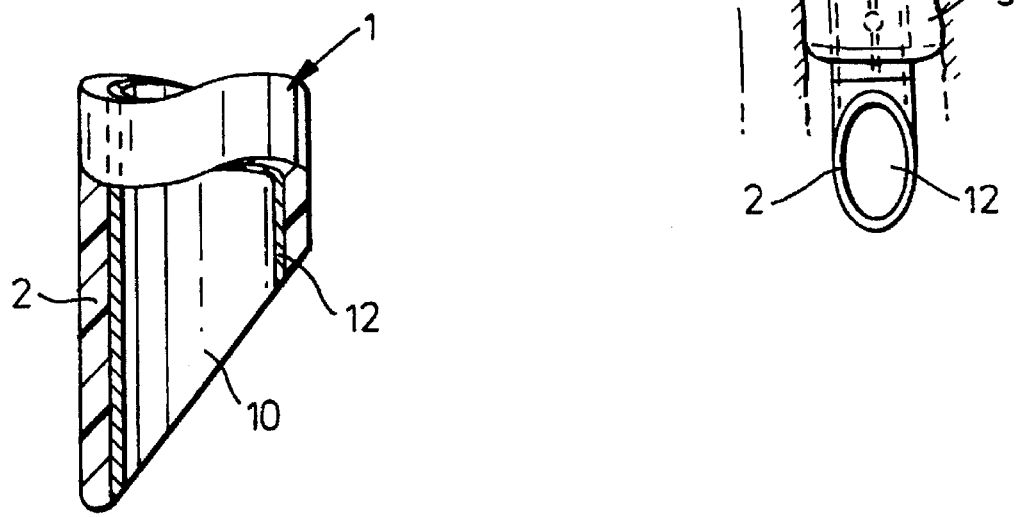
FIG. 2 is a sectional side elevation of the patient end of the tube to a larger scale.

The tube 1 is an endotracheal tube shaped to be inserted via a patient's mouth with its patient end 2 located in the trachea. The tube has a cuff 3 around its outside close to its patient end, which can be inflated via an inflation tureen 4 extending rearwardly from the cuff in the wall of the tube. The inflation lumen 4 joins with an inflation line 5, close to the machine end 6 of the tube, and is terminated by an inflation indicator balloon 7 and a combined valve and connector 8. The main body of the tube is made of PVC and it has an open bore 10 extending along its length. At its machine end 6, a connector (not shown) is inserted in the bore 10 for making connection to the tube by ventilation tubing or the like (not shown). As so far described, the tube is of conventional construction.

On the inside of the tube 1, that is, along its bore 10, the tube is coated with a layer 12 of lysozyme. Lysozyme is an enzyme that kills bacteria. The layer 12 need not be entirely of lysozyme but could comprise another substance in addition to lysozyme. Other enzymes effective to reduce the build-up of bacteria could alternatively, or additionally, be used. The layer could also extend along the outside of the tube 1 to reduce the risk of infection from secretions that collect in the trachea outside the tube, above the cuff 3. In this respect, it may only be necessary for the enzyme layer to be applied to that part of the tube above the cuff.

Where the enzyme layer is used on a urethral catheter it preferably extends along the outside of the catheter, as well as, or instead of, on the inside. This can be effective to reduce the spread of infection, which could otherwise become a systemic infection.

The enzyme or enzyme-containing substance can be coated on the tube in any of the well-known ways for securing enzymes to plastics, such as described in, for example, U.S. Pat. No. 5,244,654, U.S. Pat. No. 4,764,466, U.S. Pat. No. 4,378,435 and FR-A-2513128. These publications describe the use of antithrombogenic enzymes on tubes for use in blood vessels to reduce the risk of clotting; there is no teaching that enzymes be used in tracheal tubes or that lysozyme or other enzymes be used be reduce the accumulation of bacteria on the surface of a medico-surgical device.

The lysozyme layer is effective to reduce the rate at which bacteria can accumulate on the inside of the tube, thereby prolonging the safe life of the tube. Because the accumulation of biofilm is reduced, there is less risk of biofilm building up to a thickness where the film becomes too heavy to cling to the tube and a part becomes dislodged, falling into the patient's respiratory system. The risk of pulmonary infection from this source can, therefore, be reduced. The enzyme layer can also be effective to reduce the risk of bladder or systemic infection, according to the application in which the enzyme layer is used. Devices according to the present invention can, furthermore, be left in place longer than was previously possible, thereby reducing the discomfort to the patient of removing and replacing the device. It can also save the time of medical personnel.

What I claim is:

1. A tracheal tube having a surface layer of a substance containing an enzyme effective to reduce the build-up of bacteria on the tube from respiratory secretions.

2. A tracheal tube according to claim 1, wherein said surface layer is a coating on the inside of said tube.

3. A tracheal tube according to claim 1, wherein said tracheal tube has a cuff around the outside of the tube close to a patient end, and wherein said surface layer extends along an outside surface of said tube at least above said cuff so as to reduce the build-up of bacteria in the trachea above said cuff.

4. A tracheal tube according to any one of claims 2, 3 or 1, wherein said enzyme includes lysozyme.

* * * * *